United States Patent [19]
Zimmon

[11] Patent Number: 6,071,248
[45] Date of Patent: Jun. 6, 2000

[54] APPARATUS FOR SERIAL COLLECTION, STORAGE AND PROCESSING OF BIOPSY SPECIMENS

[75] Inventor: David S. Zimmon, Port Washington, N.Y.

[73] Assignee: Zimmon Science Corp., Port Washington, N.Y.

[21] Appl. No.: 09/197,373

[22] Filed: Nov. 20, 1998

Related U.S. Application Data

[63] Continuation-in-part of application No. 08/936,145, Sep. 22, 1997, Pat. No. 5,980,468.

[51] Int. Cl.⁷ ........................................................ A61B 5/00
[52] U.S. Cl. ............................................................ 600/566
[58] Field of Search .................................... 600/564–567, 600/569, 572; 606/167, 170, 184

[56] References Cited

U.S. PATENT DOCUMENTS

| | | | |
|---|---|---|---|
| 3,732,858 | 5/1973 | Banko | 600/566 |
| 4,586,604 | 5/1986 | Alter | 600/569 |
| 5,292,310 | 3/1994 | Yoon | 600/566 |
| 5,535,754 | 7/1996 | Doherty | 600/564 |
| 5,542,432 | 8/1996 | Slater et al. | 600/564 |
| 5,649,547 | 7/1997 | Ritchart et al. | 600/566 |
| 5,782,747 | 7/1998 | Zimmon | 600/104 |
| 5,871,454 | 2/1999 | Majlessi | 600/564 |

*Primary Examiner*—Max Hindenburg
*Attorney, Agent, or Firm*—Collard & Roe, P.C.

[57] ABSTRACT

An apparatus for performing a medical procedure comprising an elongated shaft having multiple apertures extending therethrough. The shaft has a proximal end and a distal end. An actuator is positioned within the aperture and has a proximal end and an opposite distal end. A spring jaw is connected to the distal end of the actuator for cutting and collecting biopsy specimens. The spring jaw is closed by advancing the shaft over the jaw while holding the actuator in place. This action cuts the biopsy specimen without moving the cutting jaw away from the desired biopsy site, thus facilitating multiple biopsies. Multiple methods for moving the biopsies from the spring jaw into the storage chamber include facilitated suction by entraining air and fluid through the perforated biopsy jaws and fluid injection from the distal shaft into the jaws that entrains the biopsies as it exits proximally through perforations in the storage chamber. Biopsies within the chamber are constrained by a constriction in the spring jaw that forms as the jaws are opened for each subsequent biopsy. After serial acquisition of several biopsies, the holding segment of the tube shaft is separated from the remainder and is closed by a cap to form a processing cassette. The cassette holds the specimens in order of acquisition through fixation and processing, to be opened for slicing or analysis.

5 Claims, 3 Drawing Sheets

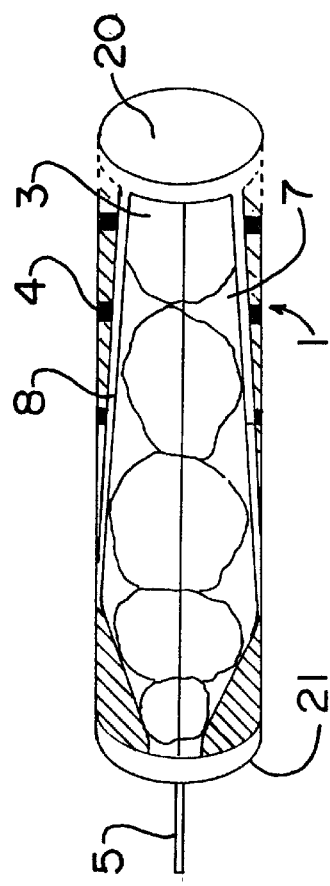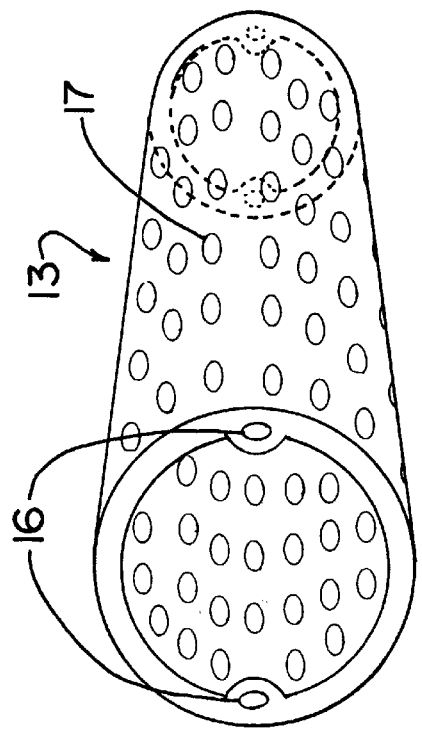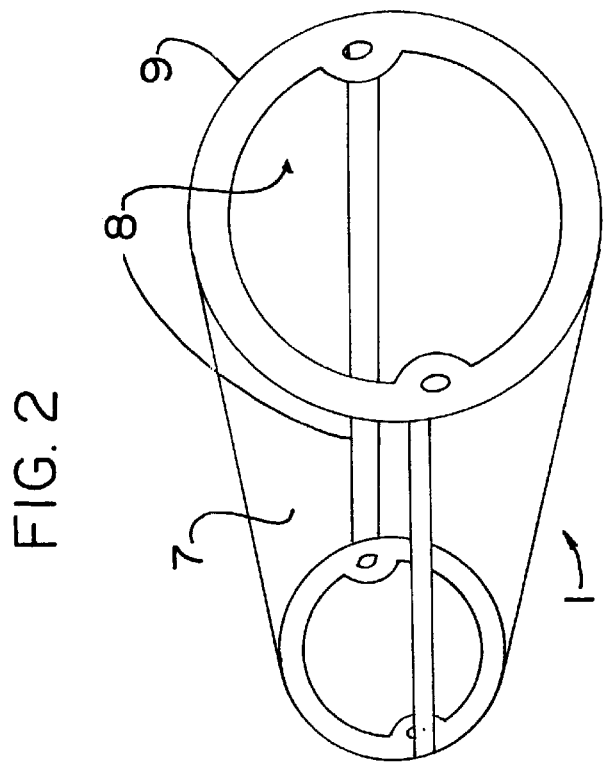

APPARATUS FOR SERIAL COLLECTION, STORAGE AND PROCESSING OF BIOPSY SPECIMENS

This application is a continuation-in-part of U.S. patent application Ser. No. 08/936,145, filed on Sep. 22, 1997, now U.S. Pat. No. 5,980,468.

BACKGROUND OF THE INVENTION

1. Field of the Invention

The present invention relates to improved design and construction of a multipurpose medical instrument for serial collection, storage and processing of biopsy specimens.

2. The Prior Art

Capture, serial collection and storage for processing in a cassette portion of a biopsy apparatus is a complex process requiring precision of many related operations. In addition, these operations are reduced to a small scale in biopsy devices that must traverse access sites or endoscopes with operating channels ranging from 3 to 0.5 mm. Multiple specimens must be retrieved in sequence without mixing them to ensure that the site of biopsy is known and to minimize the number of instrument passes through the access passage or endoscope to the biopsy site.

The storage and processing of multiple specimens within a biopsy instrument yields a great savings of time and effort in processing the biopsies, as well as preventing specimen loss or damage during handling. This goal is facilitated by applying redundant methods for forcing the minute biopsy specimens into a storage cassette of the biopsy instrument and by minimizing the operating parts of the biopsy instrument to maximize the storage volume.

The prior art described in the spring based multipurpose medical instrument in U.S. Pat. No. 5,782,747, the disclosure of which is herein incorporated by reference, obviates the use of cumbersome metal shafts and coverings that occupy the space needed for specimen storage. Standard jaw fulcrum biopsy devices require a stiff shaft to prevent kinking and binding within the endoscope when the actuator cable(s) is pulled to close the biopsy jaws and then held to maintain jaw closure when removing the device and biopsy from the endoscope or access passage. The combined stiffness of the shaft and pull on the actuator cable(s) straightens the biopsy device and endoscope. This action moves the endoscope and biopsy device away from the biopsy site and limits maneuverability. This stiffness and uncontrolled motion also risks trauma to the biopsy site and limits access in curved lumens. A further limitation of stiff shafts is that they reduce the options for carrier instrument flexibility and maneuverability. The present invention solves these problems in a unique and unobvious way.

SUMMARY OF INVENTION

It is therefore an object of the present invention to overcome the drawbacks of the prior art and provide an improved medical instrument that is capable of the serial collection, storage and processing of biopsy specimens.

One embodiment of the present invention provides an instrument for performing a medical procedure of the type disclosed in the spring based multipurpose medical instrument shown in U.S. Pat. No. 5,782,747, the disclosure of which is herein incorporated by reference. This device uses a simple plastic tube shaft over a spring-based jaw. The jaw opens when a slidable flexible cable pushes the jaw out of the distal shaft or the tube shaft is pulled back. Release from the tube shaft constraint opens the spring jaw. The spring jaw is closed by advancing the tube shaft a short distance of 5 to 10 mm to recapture and close the jaw.

The absence of the stiff shaft and taut actuator cable required to open and close a fulcrum jaw device allows the spring based medical instrument to be flexible, not inhibit maneuverability of the carrying instrument and provide space within the distal tube shaft for storage of biopsy specimens.

The device according to the invention comprises a flexible plastic shaft with one or two side lumens and a relatively large central lumen. The distal end contains a remotely controllable folded spring jaw biopsy device of the type described above within the central lumen, that is stabilized by metal or plastic guides. Plastic or metal guides are preferably inserted into the central lumen of the catheter to support and prevent twisting of the folded spring and to create a chamber for the storage of biopsies. The guides enlarge the lumen and ensure that there is sufficient room to store the collected biopsy specimens as compared to a solid plastic extrusion with only a slot as a guide. It also enables the use of a simple extruded catheter for the device. The folded spring jaw is extended proximally to form a chamber within the shaft to receive the specimens.

The junction of the chamber and the spring jaw is angulated to increase the distance between the jaws when they are extended and also to form a constriction at the distal most end of the chamber. The constriction and holding chamber remain within the shaft and prevent loss of the stored biopsies. As the spring jaws are drawn into the shaft with each new biopsy, the constriction is reduced, allowing the latest specimen to be aspirated into the holding chamber. There are side lumens(s) having open slits in the shaft to carry suction from the proximal end of the catheter to draw the specimens into the chamber after each biopsy.

Since the tube shaft or catheter is passed to the biopsy site within a loosely fitting endoscope instrument channel, it is constrained by the endoscope channel. Only the few centimeters of the biopsy device outside the distal end of the endoscope are unsupported.

Advancing the tube shaft within the constraining endoscope channel closes the jaws with little tendency to kink the tube shaft. The action of the tube shaft in moving forward to close the jaws while the flexible actuator cable is held in place ensures that the closed spring jaw remains at the desired biopsy site. This movement control facilitates multiple target biopsies with minimum repositioning the endoscope or biopsy instrument. The capture of the biopsy jaws by the tube shaft at each biopsy moves the biopsy toward the shaft and facilitates transfer of each specimen to the tube shaft storage cassette.

After the specimens have been collected, the spring jaws are removed and the distal end of the shaft is capped. The shaft is cut at a marked site proximal to the specimen holding chamber and capped with a second cap. Perforated caps allow fixation and processing of the specimens within the chamber. The shaft has thus become a processing cassette with the serial specimens enclosed in order of acquisition and ready for fixation and processing without further handling.

After processing to wax, the closed shaft is cut open and the biopsies are ready for slicing, still remaining in order of acquisition. Thus, a single log prepared at the time of biopsy serves to identify each specimen to the submitter and laboratory, and for reporting without handling, risk of biopsy loss or documentation error.

This invention has the option for use without an endoscope through a second external bendable tube shaft. The external tube shaft may be plastic, metal or any bendable material. The operator forms and inserts the tube shaft into the biopsy site. A spring based biopsy instrument of chosen diameter and flexibility is passed through the outer shaft to perform a biopsy or other operation. Operation of this invention may be monitored radiologically, visually, by palpation or any alternative.

One embodiment of the improved design for the cutting biopsy jaws is to provide multiple perforations in the spring metal jaw. The perforations allow air or fluid injected through the endoscope to entrain the biopsy toward the proximal suction slits in the storage chamber. This entrainment adds to the suction force in propelling the biopsy proximally.

A second embodiment for moving the biopsy proximally from the jaws into the storage chamber is to forcibly inject fluid from the proximal end of the tube shaft distally into the closed jaws containing the captured biopsy. The fluid is injected through channels molded into the tube shaft. In this embodiment, there are perforations in the storage chamber that facilitate movement of the injected fluid stream back to storage chamber to entrain the biopsy proximally as the injectate exits the storage chamber through the perforations. Each successive biopsy capture and injection compresses the biopsies proximally to maximize the number of biopsies stored and to prevent mixing.

These operations are facilitated by the capture of the biopsy jaws by the shaft with each closure. Perforations in the storage chamber also accelerate the access of fixative and processing fluid when the storage cassette is cut from the shaft for fixation and prepared for analysis. In a large diameter instrument, biopsies could by forced proximally through the entire tube shaft to exit at a side port and return to the operator for immediate inspection and analysis, instead of using the caps described above.

Related objects and advantages of the present invention will be apparent from the following description of the drawings.

BRIEF DESCRIPTION OF THE DRAWINGS

In the drawings, wherein similar reference numbers indicate similar elements throughout the several views:

FIG. 2 shows a perspective view of the tube shaft extrusion with two suction slits within the storage chamber;

FIG. 3 shows a side cross sectional view of the apparatus according to the invention after the shaft is cut and capped;

FIG. 5 shows the perforated storage chamber of the tube shaft extrusion with fluid injection channels molded into the shaft according to the embodiment of FIG. 4.

DETAILED DESCRIPTION OF THE PREFERRED EMBODIMENTS

Figure 1:
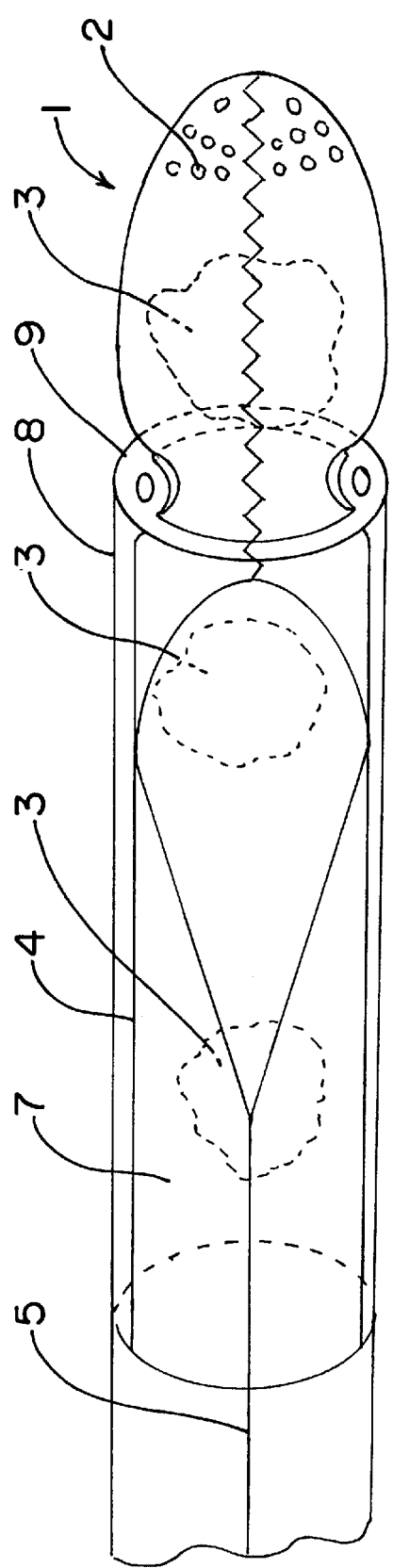
FIG. 1 shows a side view in partial cross section of the instrument according to the invention.

For the purposes of promoting an understanding of the principles of the invention reference will now be made to the embodiments illustrated in the drawings and specific language will be used to describe the same. It will be nevertheless understood that no limitation of the scope of the invention is thereby intended, such alterations and further modifications in the illustrated device, and such further applications of the principles of the invention as illustrated therein being contemplated as would normally occur to one skilled in the art to which the invention relates.

Turning in detail to the drawings, FIG. 1 shows the spring jaw 1 with a perforated tip 2 closed after cutting the biopsy specimen 3 by advancing the tube shaft 4 over the spring jaw 1 with the actuator 5 held stationary to prevent movement of the jaws during biopsy. Aspiration of air or fluid from the endoscope (not shown) passes through the perforations 2 to entrain the specimen 3 proximally into the storage chamber 7. Each additional biopsy occludes the most proximal suction slits 8 to hold the biopsies in the proximal portion of the storage chamber 7 and accentuate suction in the distal suction slits 8. When the storage chamber 7 is filled with biopsies, the suction slits 8 are blocked by biopsy specimens and the operator is unable to aspirate fluid or air. This signals to the operator that the storage chamber 7 is filled and the instrument should be retrieved.

FIG. 2 shows the distal tube shaft extrusion with suction slits 8.

After all of the specimens have been collected, spring jaws 1 are removed and storage chamber 7 is cut and capped as shown in FIG. 3. Caps 20 and 21 are placed over the distal and proximal ends, respectively, of storage chamber 7 to create a processing cassette for biopsy specimens 3.

Figure 4:
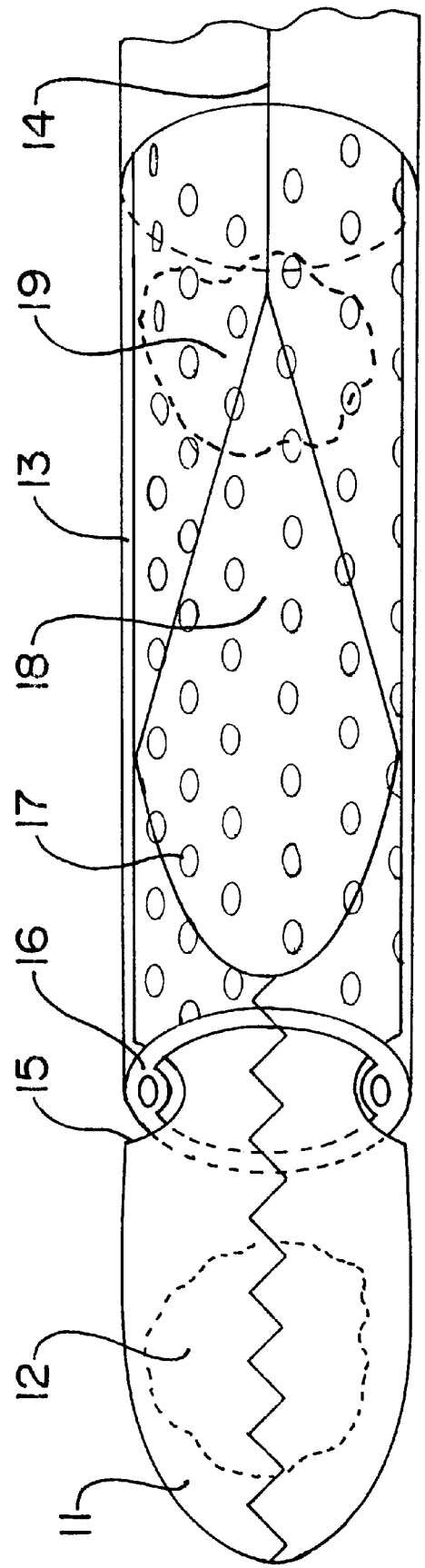
FIG. 4 shows a side view in partial cross section of an alternative embodiment of the invention.

FIG. 4 illustrates an alternative embodiment of the invention, in which spring jaw 11 does not have perforations. The tip of spring jaw 11 is closed after cutting the biopsy specimen 12 by advancing the tube shaft 13 over the spring jaw 11 with the actuator 14 held stationary. A slot 15 in the spring jaw passes injected fluid to the jaw tip. Fluid injected into the jaw 11 through the channels 16 molded into the tube shaft 13 passes out of the perforations 17 in the storage chamber 18, forcing the biopsy specimen 19 into the storage chamber 18. Each successive biopsy and fluid injection forces the biopsies sequentially into the biopsy chamber aligned in order of acquisition. The length of the storage chamber determines the number of biopsies held. the location of the storage chamber within the flexible tube shaft does not limit flexibility of the biopsy device, allows a full range of endoscope movement and provides a large space for serial biopsy storage.

Specimen fixation and processing are facilitated by fluid access through the storage chamber perforations 17. Alternatively, the fixative may be injected directly through the channels 15 in the tube shaft 13. After processing, the specimens are recovered by removing the spring jaw 11 and opening the storage chamber 18 containing the biopsies in acquisition sequence.

FIG. 5 shows another view of the tube shaft extrusion 13 with perforations 17 in the storage chamber 18, having molded fluid channels 16. Caps such as those shown in FIG. 3 can be placed over the ends of storage chamber 18 to create a processing cassette if the biopsies are not to be used immediately.

What is claimed is:

1. An apparatus for performing a medical procedures, comprising:

an elongated shaft having a central lumen extending longitudinally therethrough, said shaft having a proximal and a distal end and forming a storage chamber for the storage of biopsy specimens, said shaft having proximally accessed side lumens to act as a suction means and draw biopsy specimens into the storage chamber in order of acquisition;

an actuator positioned within said central lumen and having a proximal end and a distal end;

a spring jaw having two jaw members with a cutting tool disposed thereon, said spring jaw being connected to the distal end of the actuator for cutting and collecting biopsy specimens, said spring jaw being remotely deployable by extending and retracting the shaft; and a cap positionable over each end of the shaft, said caps closing said shaft for storage and processing of biopsy specimens collected by the biopsy means.

2. The apparatus according to claim 1, wherein the spring jaw is perforated to aid in suction by aspirating air and fluid injected into the storage chamber to entrain the biopsy specimens in to the storage chamber.

3. The apparatus according to claim 1, wherein the side lumens are connected to the central lumen.

4. The apparatus according to claim 1, wherein the side lumens are connected to the spring jaw and wherein the storage chamber is perforated.

5. An apparatus for performing a medical procedures, comprising:

an elongated shaft having a central lumen extending longitudinally therethrough, said shaft having a proximal and a distal end and forming a perforated storage chamber for the storage of biopsy specimens, said shaft having proximally accessed side lumens, to act as a suction means and draw biopsy specimens into the storage chamber in order of acquisition;

an actuator positioned within said central lumen and having a proximal end and a distal end;

a spring jaw having two jaw members with a cutting tool disposed thereon, said spring jaw being connected to the distal end of the actuator and the side lumens for cutting and collecting biopsy specimens, said spring jaw being remotely deployable by extending and retracting the shaft; and a cap positionable over each end of the shaft, said caps closing said shaft for storage and processing of biopsy specimens collected by the biopsy means; and a slot in the side lumens to allow fluid injected through the side lumens to enter the closed spring jaw and exit proximally through the storage chamber perforations to entrain the biopsy specimen into the storage chamber.

* * * * *